US010233103B2

(12) United States Patent
Geng et al.

(10) Patent No.: US 10,233,103 B2
(45) Date of Patent: Mar. 19, 2019

(54) ADVANCED OXIDATION PROCESS OF DEGRADING NONSTEROIDAL ANTI-INFLAMMATORY DRUGS IN SEWAGE BY UV PERSULFATE

(71) Applicant: NANJING UNIVERSITY, Nanjing (CN)

(72) Inventors: Jinju Geng, Nanjing (CN); Xingsheng Gao, Nanjing (CN); Hongqiang Ren, Nanjing (CN); Ke Xu, Nanjing (CN); Yan Zhang, Nanjing (CN); Hui Huang, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 15/626,126

(22) Filed: Jun. 18, 2017

(65) Prior Publication Data
US 2018/0265386 A1   Sep. 20, 2018

(30) Foreign Application Priority Data

Mar. 14, 2017 (CN) .......................... 2017 1 0151514

(51) Int. Cl.
| | |
|---|---|
| *C02F 9/00* | (2006.01) |
| *G01N 30/72* | (2006.01) |
| *B01D 15/30* | (2006.01) |
| *B01D 15/42* | (2006.01) |
| *C02F 101/34* | (2006.01) |

(Continued)

(52) U.S. Cl.
CPC .............. *C02F 9/00* (2013.01); *B01D 15/305* (2013.01); *B01D 15/426* (2013.01); *G01N 30/7233* (2013.01); *C02F 1/325* (2013.01);

*C02F 1/52* (2013.01); *C02F 1/68* (2013.01); *C02F 1/72* (2013.01); *C02F 1/725* (2013.01); *C02F 2001/007* (2013.01); *C02F 2101/322* (2013.01); *C02F 2101/34* (2013.01); *C02F 2101/38* (2013.01); *C02F 2103/005* (2013.01); *C02F 2201/322* (2013.01); *C02F 2209/00* (2013.01);

(Continued)

(58) Field of Classification Search
None
See application file for complete search history.

(56) References Cited

FOREIGN PATENT DOCUMENTS

EP     2610221    *  2/2012

* cited by examiner

*Primary Examiner* — Sheng H Davis
(74) *Attorney, Agent, or Firm* — W&K IP

(57) ABSTRACT

The present invention discloses an advanced oxidation process of degrading nonsteroidal anti-inflammatory drugs in sewage by UV persulfate. The sewage flows to a secondary sedimentation tank by gravity, and sediments are precipitated and separated. $Na_2S_2O_8$ solution is added therein, and a UV lamp is opened. Effluent result is analyzed after photooxidation. The sewage is transferred into a contact disinfection pool to react with $ClO_2$ before discharging safely. The present invention uses a UV-based advanced oxidation process, which can effectively remove the nonsteroidal anti-inflammatory drugs in sewage, meets the requirements of sewage discharging, and decreases the environmental risk of nonsteroidal anti-inflammatory drugs. The method has some advantages such as simple equipments, easy operation, reasonable economy, as well as efficient treatment effect and high stability.

7 Claims, 3 Drawing Sheets

(51) Int. Cl.
*C02F 101/38* (2006.01)
*C02F 103/00* (2006.01)
*C02F 1/52* (2006.01)
*C02F 1/72* (2006.01)
*C02F 1/00* (2006.01)
*C02F 1/32* (2006.01)
*C02F 1/68* (2006.01)
*C02F 101/32* (2006.01)

(52) U.S. Cl.
CPC ...... *C02F 2303/04* (2013.01); *C02F 2305/02* (2013.01)

ADVANCED OXIDATION PROCESS OF DEGRADING NONSTEROIDAL ANTI-INFLAMMATORY DRUGS IN SEWAGE BY UV PERSULFATE

CROSS-REFERENCE TO RELATED APPLICATIONS

This application claims priority to Chinese Patent Application No. 201710151514.0 with a filing date of Mar. 14, 2017. The content of the aforementioned application, including any intervening amendments thereto, are incorporated herein by reference.

TECHNICAL FIELD

The present invention relates to the technical field of treatment of nonsteroidal anti-inflammatory drugs, and more particularly to, an advanced oxidation process of degrading nonsteroidal anti-inflammatory drugs in sewage by UV persulfate.

BACKGROUND OF THE PRESENT INVENTION

Nonsteroidal anti-inflammatory drugs are the most widely used anti-inflammatory drugs in clinical practice, which are the second most consuming drugs less than anti-infective drugs in China every year. According to chemical structure, nonsteroidal anti-inflammatory drugs can be divided into the following categories: formic acid, such as aspirin; acetic acid, such as diclofenac and indomethacin; propionic acids, such as ibuprofen and naproxen; oxicams, such as piroxicam and meloxicam; coxibs, such as celecoxib and rofecoxib; pyrazolones, such asbutazodine, aminopyrine; others, such as nimesulide. These drugs can not be absorbed completely by human body after being taken, and the rest will be released into the environment with urine and faeces. Sewage treatment plants are main gathering sites. As a new type of pollutant, the existing toxicity studies have shown that the nonsteroidal anti-inflammatory drugs bring ecological toxicity on *Zebrafish, Oryzias Latipe, Daphnia Magna* and *Lemnaceae* or other aquatic organisms. The extensive use and abuse of drugs make the substance and its active components input into aquatic environment continuously. Properties of drugs (optical activity, half volatility, polarity and high toxicity etc.) and evolution law of the aquatic environment determine that the substances will transmit and spread for a long distance, then forming a universal accumulation. Thus it poses an uncertain potential threaten to human health because of the uncertainty. Therefore, it attracts more and more interests on how to remove nonsteroidal anti-inflammatory drugs in sewage treatment, systems effectively.

Study shows that the nonsteroidal anti-inflammatory drugs can not be removed from the sewage with traditional treatment techniques in sewage treatment plants, thus the drugs flow into aquatic environment along with tail water of the sewage, plant continuously and accumulate universally, and effect on aquatic ecosystems in a long time. It poses a potential threaten to aquatic environment, further influences drinking water quality directly or indirectly, and does harm to human health.

An advanced treatment process of sewage is considered as an important step of guaranteeing safe discharge of sewage. It is very important to study variety of sewage treatment technologies for removing effects on nonsteroidal anti-inflammatory drugs. Some advanced treatment processes such as activated carbon adsorption, coagulation precipitation, chlorination, can not get satisfied removal effect. For example, hydrogen peroxide has no effect on removing nonsteroidal anti-inflammatory drugs. Ozone has limited effect under present ozone dose and contact time in sewage treatment plants, and it can only remove nonsteroidal anti-inflammatory drugs partially. There is no systematic study on the use of UV-based advanced oxidation process to remove nonsteroidal anti-inflammatory drugs in actual sewage yet.

SUMMARY OF PRESENT INVENTION

An advanced oxidation process of degrading nonsteroidal anti-inflammatory drugs in sewage by UV persulfate is provided, it mainly comprises steps of:

1) the sewage flowing to a secondary sedimentation tank by gravity, and sediments being precipitated and separated therein, detecting and recording concentration of the nonsteroidal anti-inflammatory drugs remaining in supernatant;

2) adding $NaS_2O_8$ solution separated in the secondary sedimention tank with mass concentration of 50~70% into supernatant, and making sure the molar ratio of $NaS_2O_8$ and nonsteroidal anti-inflammatory drugs from 1:1 to 100:1, then transferring the reaction solution to an optical reactor for reacting and irradiating the solution for 5~10 mins with UV light having a working power of 22 Watt, and keeping all the components of the reaction solution with a uniform concentration by eiectromagenic stirring.

3) analyzing the result of the solution after the reaction of step 2), detecting the concentration of nonsteroidal anti-inflammatory drugs using UPLC-MS, and calculating the removal rate and setting up dynamic simulation and then transferring the effluent into a contact disinfection tank to react with $ClO_2$ for disinfecting and killing pathogenic Microbes before discharging the effluent therefrom.

Further, the secondary sedimentation tank is a vertical sedimentation tank with circular section, and the sewage flows from top to bottom with velocity of 15-25 mm/s, and spiral baffles are disposed at the bottom to distribute the sewage uniformly with rising speed of 0.6-0.8 malls at water passing section and setting time of 1.5-15 h; suspended solids sank into a cone sludge bucket, and clean water overflows out from all around the bucket along a overflow weir, baffles and scum tank are disposed above the weir to intercept scum and ensure effluent quality; and a sludge pipe with diameter of 300-400 mm is disposed near the tank wall, a sludge is discharged regularly by hydrostatic pressure.

Further, detecting method of the concentration of the nonsteroidal anti-inflammatory drugs has steps as follows:

1) sample extraction: sampling 500 mL water sample filtered with 0.22 mixed fibre membrane, and then storing the sample in a refrigerator of 4° C. for solid phase extraction and concentration detection of the nonsteroidal anti-inflammatory drugs afterward, and repeating each test three times and analyzing average values±standard deviation (SD);

2) sample purification: extracting solid phase extraction column of CNW HLB of aqueous phase (60 mg, 3 mL), i.e., organic balance column, and specific steps as follows:

a. balancing the CNW HLB column by adding 3 mL methanol;

b. washing the CNW HLB column with 3 mL pure water;

c. 50 mL water sample passing through the CNW HLB column at a flow rate of 5 mL/min;

d. washing the CNW HLB column again with 3 mL methanol (5%);

e. elutanting with 6 mL methanol solution, and drying liquid nitrogen to 1 mL, and storing in a refrigerator of 4° C. until subsequent machine inspection;

3) detecting the concentration of nonsteroidal anti-inflammatory drugs by UPLC-MS: the UPLC-MS being operated in an electrospray negative (ESI) mode, data acquisition being performed by multiple reaction monitoring (MRM), separation being performed using a ACQUITY UPLC BEH-C18 chromatographic column (2.1*50 mm, 1.7 μm,) at 30° C. with isocratic elution, the mobile phase being pre-ultrasonic degassed prior to use consisting of water (A) and methanol (B) at a flow rate of 0.1 mL/min, the isocratic elution being performed by 20% A phase and 80% B phase, isocratic elution for 5 mins and injection volume being 10 μL by an auto-injector.

Further, the removal rate of the nonsteroidal anti-inflammatory drugs equals to $(1-C_t/C_0) \times 100\%$, $C_0$ is the concentration at beginning, and $C_t$ is the concentration of the nonsteroidal anti-inflammatory drugs at reaction time of t, and the concentration unit of the nonsteroidal anti-inflammatory drugs is ug/L.

Further, the optical reactor is made of quartz glass, and a quartz sleeve is vertically disposed in the center of the optical reactor; and an ultraviolet lamp is placed in the quartz sleeve for irradiation.

Further, the ultraviolet lamp is a low pressure mercury lamp which emits monochromatic ultraviolet, light of 254 nm, the intensity of, the ultraviolet light from the outer wall of the quartz tube is 1.35 MW/cm².

Further, a $ClO_2$ generator is connected with the contact disinfection tank, which is a multilevel combined $ClO_2$ reactor. The $ClO_2$ generator includes a tank reactor composed of acid proof conduit and water jet vacuum set. The tank reactor is a two-stage or multistage reactor. An air distributor is disposed in the main tank reactor, and a balance tube is disposed in the auxiliary tank reactor, so that the reaction is more complete and the discharging of reacted raffinate can meet the requirement of discharging standard. Aqueous solution or stable $ClO_2$ solution is obtained by the generated $ClO_2$. The reaction principle is that: $NaClO_3 + 2HCl = ClO_2 + \frac{1}{2}Cl_2 + NaCl + H_2O$. The reaction with $ClO_2$ can disinfect and kill pathogenic microorganisms in the sewage, and discharge the effulant of the contact disinfection tank eventually.

Advantages of this Invention

1. Free sulfate radical (—$SO_4^-$) with high oxidation ability was released from oxidant NaS2O8 by UV-based advanced oxidation technology, which can remove nonsteroidal anti-inflammatory drugs in sewage efficiently and meet the requirement of sewage dischargement and prevent environmental solution.

2. The method of the present invention has some advantages such as simple equipments, easy operation, reasonable economy, as well as no pollution and high stability.

3. The invention makes up for the inadequacy of the sewage purification processes, improved the existing drawbacks such as low efficiency. uncertainty.

DETAILED DESCRIPTION OF PREFERRED EMBODIMENTS

Figure 1:
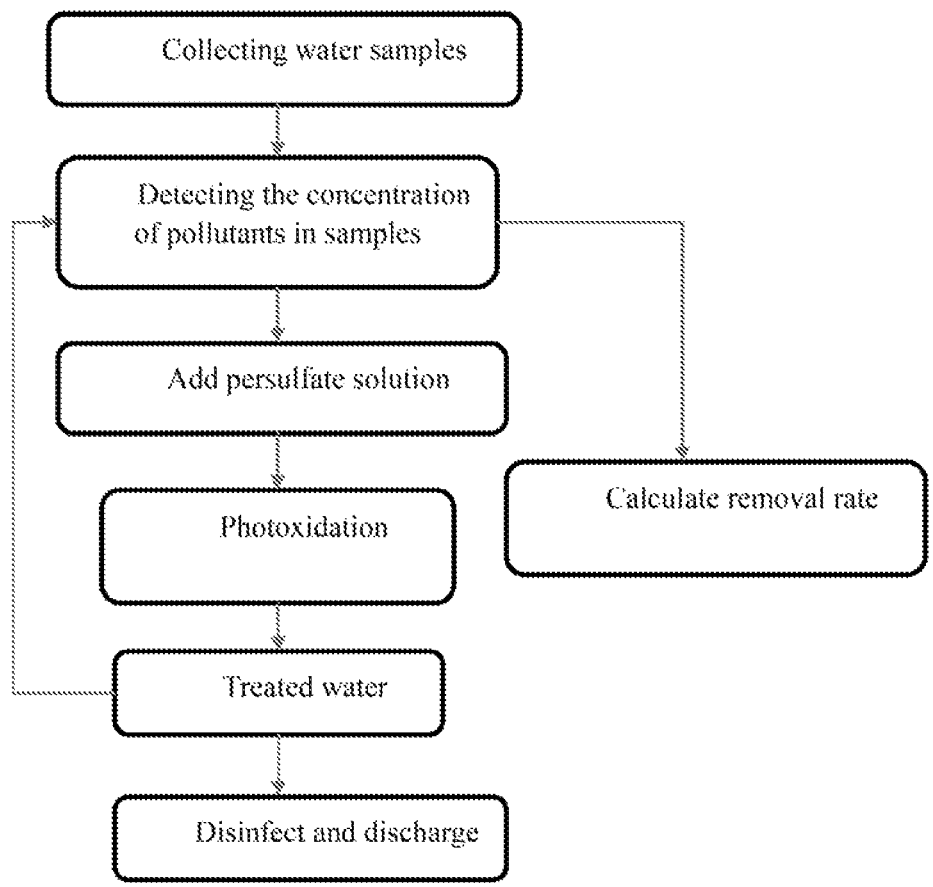
FIG. 1 is an operation flowchart of an advanced oxidation process of degrading nonsteroidal anti-inflammatory drugs in sewage by UV persulfate.

For further illustrating the invention, examples are given bellow.

Example 1

Secondary biological effluent from a municipal sewage treatment plant in a city of Nanjing was taken as an example. An advanced oxidation process for degrading nonsteroidal anti-inflammatory drugs in sewage by UV persulfate mainly comprises steps that:

1) the sewage flows to a secondary sedimentation tank by gravity, and sediments are precipitated and separated therein. The secondary sedimentation tank is a vertical sedimentation tank with circular section. Sewage flows from top to bottom with the velocity of 15 mm/s. Spiral baffles are disposed at the bottom to distribute the sewage uniformly in the tank with rising speed of 0.6 mm/s at water passing section and settling time of 1.5 h. Suspended solids sank into a cone sludge bucket, and clean water overflows out from all around the bucket along a overflow weir. Baffle and scum are disposed above the weir to intercept scum and ensure water quality. A sludge pipe with diameter of 300 mm is disposed near the tank wall. Sludge is discharged regularly by hydrostatic pressure from the sludge pipe. Separated supernatant is extracted for detecting and recording the concentration of nonsteroidal anti-inflammatory drugs remaining therein using high performance liquid chromatography;

2) $NaS_2O_8$ solution separated in the secondary sedimentation tank with mass concentration of 50-70% is added into the supernatant, so that the molar ratio of $NaS_2O$ and, nonsteroidal anti-inflammatory drugs is 60:1, and reaction solution is obtained. The reaction solution is then transferred to an optical reactor for reacting to irradiate the solution for 5 mins with UV light having a working power of 22 Watt, and keeping all the components of the reaction solution with a uniform concentration by electromagenic stirring. The optical reactor is made of quartz glass. A quartz sleeve is vertically disposed in the center of the optical reactor. An ultraviolet lamp is placed in the quartz sleeve for irradiation. The ultraviolet lamp is low pressure mercury lamp, which emits monochromatic ultraviolet light of 254 nm. The intensity of the ultraviolet light from the outer wall of the quartz tube is 1.36 mW/cm².

3) The result of the solution after the reaction, of step 2) is analyzed. The concentration of nonsteroidal anti-inflammatory drugs is detected with high performance liquid chromatography. The removal rate is calculated and dynamic simulation is set up. Then the effluent is transferred into a contact disinfection tank to react with $ClO_2$ for disinfecting. A $ClO_2$ generator is connected with the contact disinfection tank, which is a multilevel combined $ClO_2$ generator. The $ClO_2$ generator includes a tank reactor composed of acid proof conduit and water jet vacuum set. The tank reactor is a two-stage or multistage reactor. An air distributor is disposed in the main tank reactor, and a balance tube is disposed in the auxiliary tank reactor, so that the reaction is more complete and the discharging of reacted raffinate can meet the requirement of the standard. Aqueous solution or stable $ClO_2$ solution is obtained by the generated $ClO_2$. The reaction principle is that: $NaClO_3+2HCl=ClO_2+½Cl_2+NaCl+H_2O$. The reaction with $ClO_2$ can disinfect and kill pathogenic microorganisms in the sewage, and discharge the effluant of the contact disinfection tank eventually.

Example 2

Secondary biological biological effluent from a municipal sewage treatment plant in a city of Nanjing was taken as an example. An advanced oxidation process for degrading nonsteroidal anti-inflammatory drugs in sewage by UV persulfate mainly comprises steps that:

1) The sewage flows to a secondary sedimentation tank by gravity, and sediments are precipitated and separated therein. The secondary sedimentation tank is a vertical sedimentation tank with circular section. Sewage flows from top to bottom with the velocity of 15 mm/s. Spiral baffles are disposed at the bottom to distribute the sewage uniformly in the tank with rising speed of 0.6 mm/s at water passing section and settling time of 1.5 h. Suspended solids sank into a cone sludge bucket, and clean water overflows, out from all around the bucket along a overflow weir. Baffle and scum are disposed above the weir to intercept scum and ensure water quality. A sludge pipe with diameter of 300 mm is disposed near the tank wall. Sludge is discharged regularly by hydrostatic pressure from the sludge pipe. Separated supernatant is extracted for detecting and recording the concentration of nonsteroidal anti-inflammatory drugs remaining therein using high performance liquid chromatography;

2) $NaS_2O_8$ solution with mass concentration of 60% is added into the supernatant after separated in the secondary sedimention tank, so that the molar ratio of $NaS_2O_8$ and nonsteroidal anti-inflammatory drugs is 50:1, and reaction solution is obtained. The reaction solution is then transferred to an optical reactor for reacting to irradiate the solution for 7.5 mins with UV light having a working power of 22 Watt, and keeping all the components of the reaction solution with a uniform concentration by electromagenic stirring. The optical reactor is made of quartz glass. A quartz sleeve is vertically disposed in the center of the optical reactor. An ultraviolet lamp is placed in the quartz sleeve for irradiation. The ultraviolet lamp is low pressure mercury lamp, which emits monochromatic ultraviolet light of 254 nm. The intensity of the ultraviolet light from the outer wall of the quartz tube is 1.35 $mW/cm^2$.

3) The result of the solution after the reaction of step 2) is, analyzed. The concentration of nonsteroidal anti-inflammatory drugs is detected with high performance liquid chromatography. The removal rate is calculated and dynamic simulation is set up. Then the effluent is transferred into a contact disinfection tank to react with $ClO_2$ for disinfecting, A $ClO_2$ generator is connected with the contact disinfection tank, which is a multilevel combined $ClO_2$ generator. The $ClO_2$ generator includes a tank reactor composed of acid proof conduit and water jet vacuum set. The tank reactor is a two-stage or multistage reactor. An air distributor is disposed in the main tank reactor, and a balance tube is disposed in the auxiliary tank reactor, so that the reaction is more complete and the discharging of reacted raffinate can meet the requirement of the standard. Aqueous solution, or stable $ClO_2$ solution is obtained by the generated $ClO_2$. The reaction principle is that: $NaClO_3+2HCl=ClO_2+½Cl_2+NaCl+H_2O$. The reaction with $ClO_2$ can disinfect and kill pathogenic microorganisms in the sewage, and discharge the effluant of the contact disinfection tank eventually.

Example 3

Secondary biological effluent from a municipal sewage treatment plant in a city of Nanjing was taken as an example. An advanced oxidation process for degrading nonsteroidal anti-inflammatory drugs in sewage by UV persulfate mainly comprises steps that:

The sewage flows to a secondary sedimentation tank by gravity, and sediments are precipitated and separated therein. The secondary sedimentation tank is a vertical sedimentation tank with circular section. Sewage flows from top to bottom with the velocity of 15 m/s. Spiral baffles are disposed at the bottom to distribute the sewage uniformly in the tank with rising speed of 0.6 mm/s at water passing section and settling time of 1.5 h. Suspended solids sank into a cone sludge bucket, and clean water overflows out from all around the bucket along a overflow weir. Baffle and scum are disposed above the weir to intercept scum and ensure water duality A sludge pipe with diameter of 300 mm is disposed near the tank wall. Sludge is discharged regularly by hydrostatic pressure from the sludge pipe. Separated supernatant is extracted for detecting and recording the concentration of nonsteroidal anti-inflammatory drugs remaining therein using high performance liquid chromatography;

2) $NaS_2O_8$ solution separated in the secondary sedimention tank with mass concentration of 70% is added into the supernatant so that the molar ratio of $NaS_2O_8$ and nonsteroidal anti-inflammatory drugs is 100:1, and reaction solution is obtained. The reaction solution is then transferred to an optical reactor for reacting to irradiate the solution for 10 mins with UV light having a working power of 22 Watt, and keeping all the components of the reaction solution with a uniform concentration by electromagenic stirring. The optical reactor is made of quartz glass. A quartz sleeve is vertically disposed in the center of the optical reactor. An ultraviolet lamp is placed in the quartz sleeve for irradiation. The ultraviolet lamp is low pressure mercury lamp, which emits monochromatic ultraviolet light of 254 nm. The intensity of the ultraviolet light from the outer wall of the quartz tube is 1.35 $mW/cm^2$.

3) The result of the solution after the reaction of step 2) is analyzed. The concentration of nonsteroidal anti-inflammatory drugs is detected with high performance liquid chromatography The removal rate is calculated and dynamic simulation is set up. Then the effluent is transferred into a contact disinfection tank to react with $ClO_2$ for disinfecting, A $ClO_2$ generator is connected with the contact disinfection tank, which is a multilevel combined $ClO_2$ generator. The $ClO_2$ generator includes a tank reactor composed of acid proof conduit and water jet vacuum set. The tank reactor is a two-stage or multistage reactor. An air distributor is disposed in the main tank reactor, and a balance tube is disposed in the auxiliary tank reactor, so that the reaction is more complete and the discharging of reacted raffinate can meet the requirement of the standard. Aqueous solution, or stable $ClO_2$ solution is obtained by the generated $ClO_2$. The reaction principle is that: $NaClO_3+2HCl=ClO_2+½Cl_2+NaCl+H_2O$. The reaction with $ClO_2$ can disinfect and kill pathogenic microorganisms in the sewage, and discharge the effulant of the contact disinfection tank eventually.

It should be noted that the value range involved in the above examples can be realized. Other values will not be listed hereby because of limited description.

1. result interpretation of embodiments 1) 500 mL water sample is filtered with 0.22 μm mixed fibre membrane, and then stored in a refrigerator of 4° C. for solid phase extraction and concentration detection of the nonsteroidal anti-inflammatory drugs afterward. Each test is repeated three times, and average values±standard deviation (SD) is analyzed. A simple test flowchart is shown in FIG. 1.

2) enrichment and purification of three nonsteroidal anti-inflammatory drugs solid phase extraction column of CNW HLB of aqueous phase (60 mg, 3 mL), i.e., organic balance column, is extracted. The specific steps are as follows:

a. balancing the CNW HLB column by adding 3 mL methanol;

b. washing the CNW HLB column with 3 mL pure water;

c. 50 mL water sample passing through the CNW HLB column at a flow rate of 5 mL/min;

d. washing the CNVV HLB column again with 3 mL methanol (5%);

e. elutanting with 6 mL methanol solution, and drying liquid nitrogen to 1 mL, and storing in a refrigerator of 4° C. until subsequent machine inspection.

3) The concentrations of nonsteroidal anti-inflammatory drugs are detected by UPLC-MS selected from US Waters Company. The UPLC-MS is operated in an electrospray negative (ESI) mode, and data acquisition is performed by multiple reaction monitoring (MRM), Table 1 shows the monitoring parameters of the multi-reaction.

TABLE 1

Monitoring parameters of multi-reacton of nonsteroidal anti-inflammatory drugs

| Compound | Parent ion (m/z) | Daughter-ion (m/z) | Cone Voltage (V) | Collision energy (V) |
|---|---|---|---|---|
| Diclofenac | 295.9 | 214 | 21 | 30 |
| Ibuprofen | 204.7 | 160.8 | 40 | 6.5 |
| Naproxen | 231.2 | 170 | 36 | 22 |

Separation is performed by a ACQUITY UPLC BEH-C18 chromatographic column (2.1*50 mm, 1.7 μm) at 30° C. with isocratic elution. The mobile phase consists of water and methanol at a flow rate of 0.1 mL/min. The isocratic elution is performed by 20% A phase and 80% B phase, isocratic elution for 5 mins and injection volume is 10 μL by an auto-injector.

2. Analysis of the removal rate of nonsteroidal anti-inflammatory drugs The concentration unit of nonsteroidal anti-inflammatory drugs in the present invention is μg/L.

The removal rate of nonsteroidal anti-inflammatory drugs=$(1-C_t/C_0) \times 100\%$, $C_0$—the concentration at beginning, $C_t$—the concentration of nonsteroidal anti-inflammatory drugs at reaction time of t. The nonsteroidal anti-inflammatory drugs to be detected are diclofenac, ibuprofen and naproxen.

According to the results:

1) Influence of irridation time of UV on degrading of target pollutants

Figure 2:
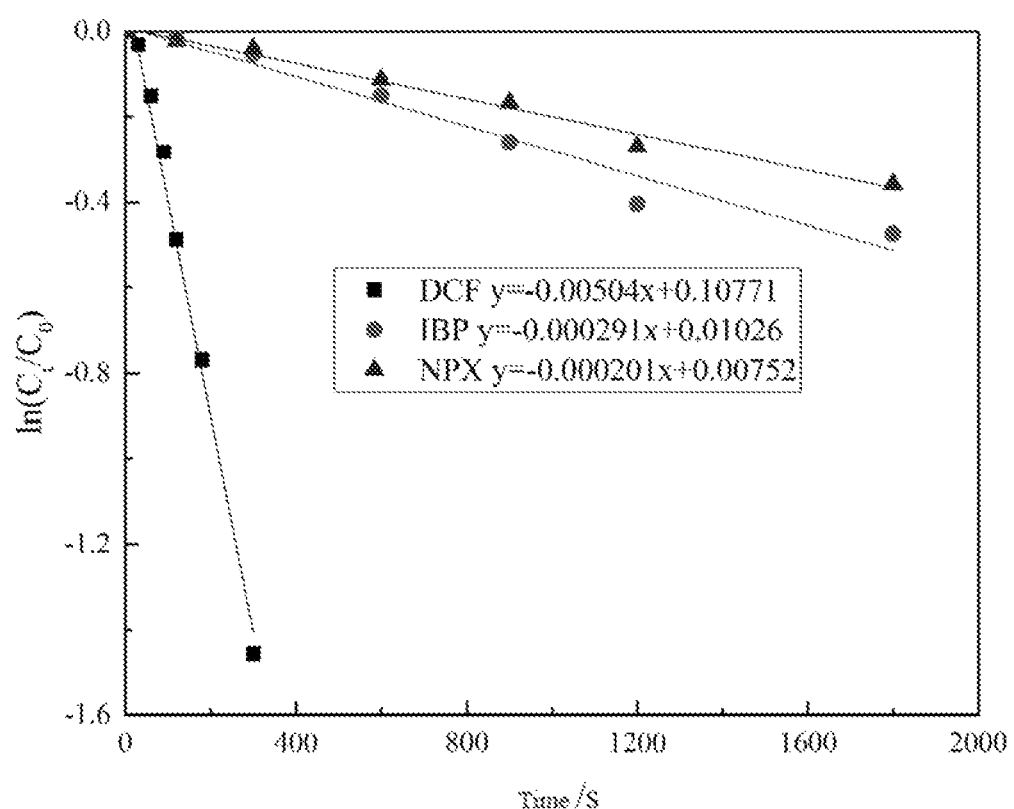
FIG. 2 illustrates influences of irridation time ondegradation effects of nonsteroidal anti-inflammatory drugs in accordance with the advanced oxidation process of degrading nonsteroidal anti-inflammatory drugs in sewage by UV persulfate of the present invention.

FIG. 2 shows the influence of irridation time on degradation effects of three nonsteroidal anti-inflammatory drugs. Diclofenac, ibuprofen and naproxen can be degraded tiredly under the Irradiation of ultraviolet, and they satisfy first order reaction kinetics, and the kinetic constants are $5.04 \times 10^{-3} s^{-1}$, $0.291 \times 10^{-3} s^{-1}$, and $0.208 \times 10^{-3} s^{-1}$.

2) Influences of molar ratio of $Na_2S_2O_8$ to nonsteroidal anti-inflammatory drugs on degrading of target pollutants.

Figure 3:
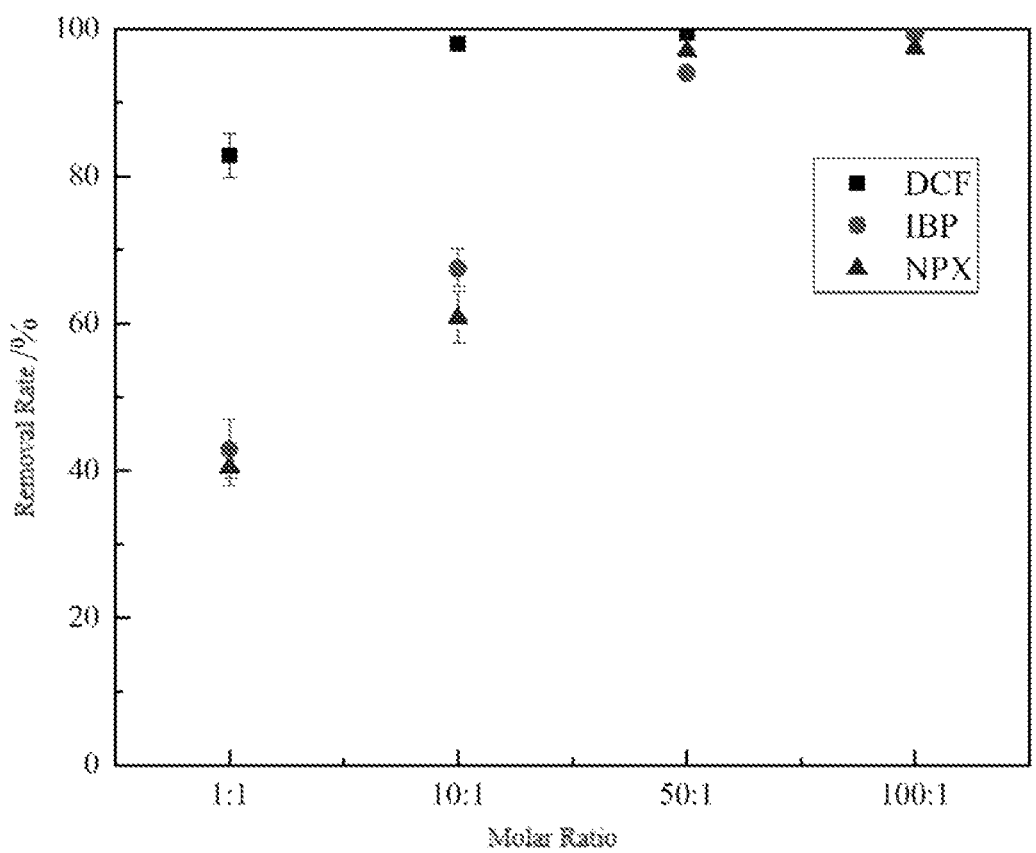
FIG. 3 illustrates influences of oxidant dose ondegradation effects of nonsteroidal anti-inflammatory drugs in accordance with the advanced oxidation process of degrading nonsteroidal anti-inflammatory drugs in sewage by UV persulfate of the present invention.

FIG. 3 shows, under 5 mins irridation of low pressure mercury lamp having a working power of 22 Watt and the molar ratio 1:1-100:1 of $Na_2S_2O_8$ to nonsteroidal anti-inflammatory drugs, the removal rates of all target polluents increase with oxidant concentration. In general, productivity of $SO_4^-$ increases when the concentration of $NaS_2O_8$ is too large, accordingly the reaction rate increases continually. The removal rate of the three nonsteroidal anti-inflammatory drugs increases with the increasing consumption of oxidant in the embodiment. Considering the removal effects in practical process, the input amount of 100:1 is selected as the best input amount. The degrading rates of the three drugs improve significantly when a $UV/NaS_2O_8$ process is used as the process of degrading nonsteroidal anti-inflammatory drugs. The removal rate can reach 95% in 5 mins.

3) influences of intensity of light sources on degrading of to pollutants

Two common ultraviolet light sources UV/AOP used in the process are selected by the test, which are respectively mercury lamp having a working power of 22 Watt and mercury lamp having a working power of 300 Watt. Removal rates of the target pollutants in condition of molar ratio (oxidant: pollutants) 100:1, irridation for 5 min are illustrated in Table 2. When the mercury lamp having the working power of 22 Watt is adopted, the removal effect of the nonsteroidal anti-inflammatory drugs is very good. Considering of energy consumption, 22 Watt UV lamp is selected as light resource.

TABLE 2

Comparison of degradation effects of nonsteroidal anti-inflammatory drugs by using two light resources

| Power of mercury lamp | Diclofenac | Ibuprofen | Naproxen |
|---|---|---|---|
| 22 W | 99.64 ± 0.1% | 96.68 ± 2.95% | 97.16 ± 1.34% |
| 300 W | 99.91 ± 0.01% | 99.38 ± 0.1% | 99.61 ± 0.55% |

In summary, the method of the present invention is effective to degrade the nonsteroidal anti-inflammatory drugs in sewage. It also demonstrated from the treatment results that the components and the parameters are both best choices to realize the method of the present invention.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. An advanced oxidation process of degrading nonsteroidal antiinflammatory drugs in sewage by UV persulfate, characterized in that it mainly comprises comprising the steps of:

1) separating supernatant from sediments from the sewage by settling and precipitating the sediments in a secondary sedimentary tank by gravity;

2) detecting and recording concentration of the nonsteroidal anti-inflammatory drugs remaining in the supernatant;
3) adding a $NaS_2O_8$ solution with mass concentration of 50-70% into the supernatant, forming a reaction solution, wherein the molar ratio of $NaS_2O_8$ and nonsteroidal anti-inflammatory drugs in the reaction solution is from 1:1 to 100:1;
4) transferring the reaction solution to an optical reactor for reacting, irradiating the reaction solution for 5-10 mins with UV light having a working power of 22 Watt, stirring the reaction solution,
5) analyzing the concentration of nonsteroidal anti-inflammatory drugs in the reaction solution after the step 4) using high performance liquid chromatography mass spectrometry (UPLC-MS), and calculating the drug removal rate and setting up dynamic simulation, and
6) transferring the reaction solution into a contact disinfection tank to react with $ClO_2$ for disinfecting before discharging therefrom.

2. The advanced oxidation process of degrading nonsteroidal anti-inflammatory drugs in sewage according to claim 1, characterized in that the secondary sedimentation tank is a vertical sedimentation tank with circular section, and the sewage flows from top to bottom with velocity of 15-25 mm/s, disposing spiral baffles at the bottom to distribute the sewage uniformly with rising speed of 0.6-0.8 mm/s at water passing section and settling time of 1.5-2.5 h; suspended solids sink into a cone sludge bucket, and clean water overflow from all around the bucket along a overflow weir, disposing baffles and scum tank above the weir to intercept scum; and disposing a sludge pipe with diameter of 300-400 mm near the tank wall, and discharging sludge regularly by hydrostatic pressure.

3. The advanced oxidation process of degrading nonsteroidal antiinflammatory drugs in sewage according to claim 1, characterized in that detecting method of the concentration of the nonsteroidal anti-inflammatory drugs comprises steps as follows:
1) sample extraction: sampling 500 mL water samples filtered with 0.22 pm mixed fibre membrane, and then storing the samples in a refrigerator of 4° C. for solid phase extraction and concentration detection of the nonsteroidal anti-inflammatory drugs afterward, and repeating each test three times and analyzing average values±standard deviation (SD);
2) sample purification: extracting solid phase extraction column of CNW HLB of aqueous phase (60 mg, 3 mL), i.e., organic balance column, and specific steps as follows:
a. balancing the CNW HTB column by adding 3 mL methanol;
b. washing the CNW HLB column with 3 mL pure water;
c. 50 mL water samples passing through the CNW HLB column at a flow rate of 5 ml/min;
d. washing the CNW HLB column again with 3 mL methanol (5%);
e. eluting with 6 mL methanol solution, and drying liquid nitrogen to 1 mL, and storing in a refrigerator of 4° C. until subsequent machine inspection,
3) detecting the concentration of nonsteroidal anti-inflammatory drugs by UPLC-MS: the UPLC-MS being operated in electrospray negative (ESI) mode, data acquisition being performed by multiple reaction monitoring (MRM), separation being performed using a ACQUITY UPLC BEH-C18 column (2.1*50 mm, 1.7 pm,) at 30° C. with isocratic elution, the selected mobile phase being pre-ultrasonic degassed prior to use consisting of water (A) and methanol (B) at a flow rate of 0.1 mL/min, the isocratic elution being performed by 20% A phase and 80% B phase, isocratic elution for 5 mins and injection volume being 10 pL by an auto-injector.

4. The advanced oxidation process of degrading nonsteroidal anti-inflammatory drugs in sewage according to claim 1, characterized in that the drug removal rate of the nonsteroidal anti-inflammatory drugs equals to $(1-C_t/C_0)\times 100\%$, wherein $C_0$ is the concentration prior to treatment, and $C_t$ is the concentration of the nonsteroidal anti-inflammatory drugs at reaction time of t, and wherein the concentration unit of the nonsteroidal anti-inflammatory drugs is ug/L.

5. The advanced oxidation process of degrading nonsteroidal anti-inflammatory drugs in sewage according to claim 1, characterized in that the optical reactor is made of quartz glass, and a quartz sleeve is vertically disposed in the center of the optical reactor; and an ultraviolet lamp is placed in the quartz sleeve for irradiation.

6. The advanced oxidation process of degrading nonsteroidal anti-inflammatory drugs in sewage according to claim 1, characterized in that the reaction is irradiated using an ultraviolet lamp comprising a quartz tube, wherein the ultraviolet lamp is a low pressure mercury lamp which emits monochromatic ultraviolet light of 254 nm, and the intensity of the ultraviolet light from the outer wall of the quartz tube is 1.35 $mW/cm^2$.

7. The advanced oxidation process of degrading nonsteroidal anti-inflammatory drugs in sewage according to claim 1, characterized in that a $ClO_2$ generator is connected with the contact disinfection tank, and the reaction with $ClO_2$ can disinfect and kill pathogenic microorganisms in the sewage.

* * * * *